(12) United States Patent
Kulkarni et al.

(10) Patent No.: US 6,495,690 B2
(45) Date of Patent: Dec. 17, 2002

(54) PROCESS FOR THE SYNTHESIS OF AN ANNULATED PYRIDINE BASE

(75) Inventors: Shivanand Janardan Kulkarni, Andhra Pradesh (IN); Kondapuram Vijaya Raghavan, Andhra Pradesh (IN); Radha Rani Vippagunta, Andhra Pradesh (IN); Srinivas Nagabandi, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/818,281

(22) Filed: Mar. 27, 2001

(65) Prior Publication Data

US 2002/0173651 A1 Nov. 21, 2002

(51) Int. Cl.[7] ...................... C07D 219/02; C07D 221/16
(52) U.S. Cl. ............................. 546/102; 546/79; 546/93
(58) Field of Search ............................. 546/102, 93, 79

(56) References Cited

U.S. PATENT DOCUMENTS 4,220,783 A * 9/1980 Chang et al.
4,675,410 A   6/1987 Feitler et al. ................ 546/251

FOREIGN PATENT DOCUMENTS

| GB | 1550726 | * | 8/1979 |
| WO | 9003366 |   | 4/1990 |
| WO | 9700861 |   | 1/1997 |

* cited by examiner

*Primary Examiner*—Bernard Dentz
(74) *Attorney, Agent, or Firm*—Ladas & Parry

(57) ABSTRACT

This invention relates to process for producing annulated pyridine bases by reacting cyclic ketones with aliphatic aldehyde in presence of ammonia in gaseous phase in the presence of a catalyst. This process provides an eco-friendly, more economical and highly selective heterogeneous method.

12 Claims, No Drawings

PROCESS FOR THE SYNTHESIS OF AN ANNULATED PYRIDINE BASE

FIELD OF INVENTION

The present invention relates to an improved process for the synthesis of an annulated pyridine base. More particularly, the present invention relates to a process for the synthesis of an annulated pyridine base over a molecular seive. The present invention particularly relates to a process for producing 1,2,3,4,5,6,7,8,-octahydroacridine by reacting cyclohexanone and formaldehyde with ammonia in gaseous phase over a molecular seive with high yields and selectivity. This invention provides a non-corrosive, eco-friendly process, where the life time of the catalyst is longer, it can be recycled and reused for many times, no-wastage of compounds (i.e. high atom selectivity) and high selectivity of the products.

BACKGROUND OF THE INVENTION

Annulated pyridines such as 9-amino-5,6,7,8 tetrahydroacridine (Tacrine) are drug intermediates for treatment of various diseases such as Alzheimer's disease, which is the most common cause of dementia in elderly people. Several methods of producing pyridine bases are known in the art such as reacting an aliphatic aldehyde and/or ketone with ammonia in gaseous phase using a solid acid catalyst such as amorphous aluminosilicate and the like, (Japanese patent application Kokai(Laid-Open) No. 63,176/76, Japanese Patent Publication Nos. 41,546/71, and 32,790/69). It is also known that crystalline aluminosilicate (zeolite) is used as the catalyst for producing pyridine bases from an aliphatic aldehyde and/or ketone and ammonia (U.S. Pat. No. 4,220,783 and Japanese patent application Kokai (Laid-Open) No. 38,362/85). These processes however, disclose preparation of only one ring pyridine compounds. The fused ring system has not yet been explored over any of these catalysts.

Increasing applications of these annulated pyridines demands an eco-friendly, economical and free handling process. The present invention provides an eco-friendly and economical process for the synthesis of a variety of these compounds.

OBJECTS OF THE INVENTION

The main object of the present invention is to provide a process for the synthesis of octahydro acridine by using a specific zeolite catalyst, which is an eco-friendly heterogeneous catalytic method.

Another object of the present invention is to improve the yield and selectivity of the product.

SUMMARY OF THE INVENTION

The present invention relates to develop a process for the preparation of octahydro acridine of the formula #1 to 9# from cyclic ketones and aliphatic aldehyde with ammonia over molecular sieves. Annulated pyridines like 9-amino-5,6,7,8 tetrahydroacridine (Tacrine) are drug molecules for treatment of various diseases like Alzheimer's disease, which is the most common cause of dementia in elderly people.

Accordingly the present invention relates to a process for the synthesis of an annulated pyridine base said process comprising reacting a cyclic ketone containing 5 to 8 carbon atoms and an aliphatic aldehyde of the formula $R_1CHO$ wherein $R_1$ is hydrogen or alkyl having 1 to 3 carbon atoms with ammonia in a gaseous phase, the mole ratio of ammonia to cyclic ketone being in the range of 0.5 to 5.0, the reaction temperature being in the range of 350° C. to 450° C., in the presence of a mesoporous sieve catalyst.

In one embodiment of the invention, the the annulated pyridine base is selected from compounds of the formula

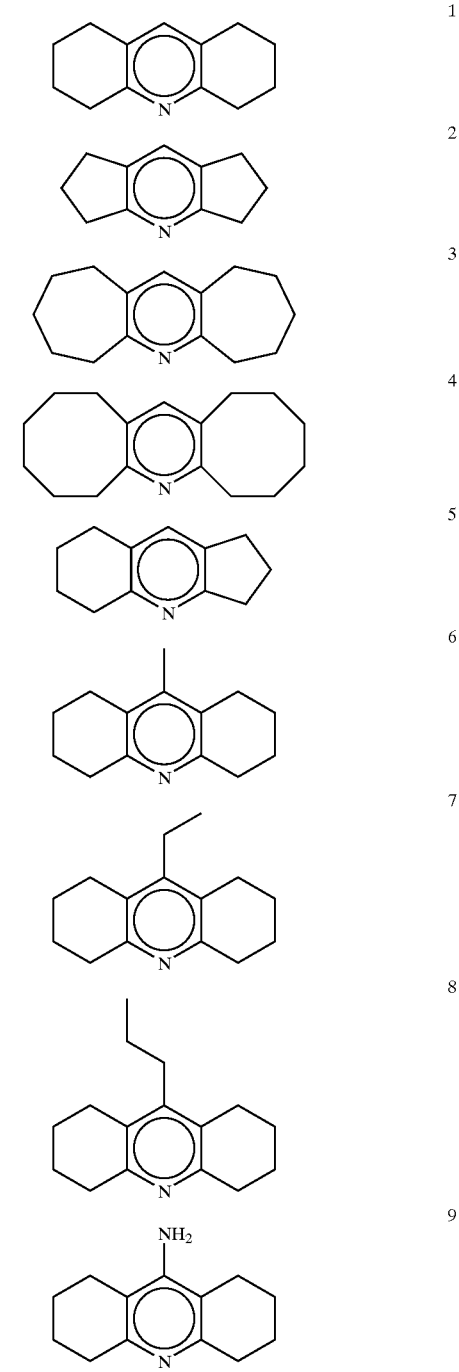

In another embodiment of the invention cyclohexanone is used as cyclic ketone and formaldehyde is used as the aliphatic aldehyde to obtain 1,2,3,4,5,6,7,8-octahydro acridine.

In another embodiment of the invention the molar ratio of cyclohexanone: formaldehyde: ammonia is 1:1:0.5-5.

In another embodiment of the invention methanol is added to the starting materials in an amount of up to 0.5 mole per mole of cyclohexanone.

In another embodiment of the invention the temperature of the reaction is in the range of 300 to 400° C.

In another embodiment of the invention acetaldehyde is used as the aliphatic aldehyde to obtain 9-methyl octahydro acridine.

In another embodiment of the invention propionaldehyde is used as the aliphatic aldehyde to obtain 9-ethyl octahydro acridine.

In another embodiment of the invention butyraldehyde is used as the aliphatic aldehyde to obtain 9-propyl octahydro acridine.

In another embodiment of the invention cyclopentanone is used as the cyclic ketone to obtain bis cyclo pentyl pyridine.

In another embodiment of the invention cycloheptanone is used as the cyclic ketone to obtain bis cycloheptyl pyridine.

In another embodiment of the invention cyclooctanone is used as the cyclic ketone to obtain bis cyclooctyl pyridine.

In another embodiment of the invention the proportion of Si to the Al in the zeolite is in the range of 2.5 to 25.

In another embodiment of the invention the catalyst is selected from the group consisting of Al-MCM41, ZSM-5, HY and H-BEA.

DETAILED DESCRIPTION OF THE INVENTION

The present invention relates to a process for producing annulated pyridines by reacting cyclic ketones and an aliphatic aldehyde with ammonia in gaseous phase in the presence of a catalyst, wherein the catalyst was obtained by commercial or synthesized.

The aliphatic cyclic ketones used in the present invention includes, cyclohexanone, cyclo pentanone, cycloheptanone and cyclooctanone and aliphtic aldehydes such as formaldehyde, acetaldehyde, propionaldehyde, butyraldehyde and formaldehyde. The combination of different cyclic ketones and aliphatic aldehydes as the starting materials determines the main compounds of the annulated pyridine to be produced. The typical examples are shown in the following Table 1.

TABLE 1

| Aldehyde | ketone | Main products formed |
|---|---|---|
| Formaldehyde | cyclo hexanone | Octahydro acridine |
| Acetaldehyde | cyclo hexanone | 9-Methyl octahydroacridine |
| Propionaldehyde | cyclo hexanone | 9-Ethyl octahydroacridine |
| Formaldehyde | cyclo pentanone | Bis bi cyclopentyl pyridine |
| Formaldehyde | cyclo heptanone | Bis bi cycloheptyl pyridine |

The reaction of the present invention may be conducted in a mode of fixed bed, fluidised bed or moving bed.

The molar ratio of ammonia to the aliphatic cyclic ketone is 0.5 to 5 mol/mol. The weight hourly space velocity (WHSV) used is 0.25 to 1.00 Hr.sup.−1. The reaction temperature is preferably 350° C. to 450° C. Although, the pressure of the reaction gases can be used in the range from below the atmospheric pressure to several atmospheric pressures, usually the pressure in the range used is atmospheric pressure.

The particularly preferable combination of a cyclic ketone and aliphatic aldehyde and ammonia for production of octahydro acridine in the molar ratio of 1:1:0.5-5.

The reaction can be effected without any trouble if the gaseous starting materials may contain water, methanol or the like. However, when acetaldehyde and formaldehyde are used as the starting materials, the amount of methanol is preferably up to 0.5 mole per mole of the acetaldehyde. Formaldehyde can be fed in a form of formalin. Further, as the aliphatic aldehyde or ketone, a dimer, a trimer, the other oligomers or polymers capable of generating a monomer of aliphatic aldehyde or ketone in an evaporator or a reactor can also be used.

Although deposition of carbon on the catalyst is detected during the reaction, the amount of the carbon deposited on the catalyst is smaller as the result of which higher yields of pyridine bases was obtained in composition with in conventional processes.

Regeneration of the catalyst is easily effected by any conventional method such as burning out the carbon deposited on the catalyst by passing air through the catalyst layer at a temperature of 450° C. to 550° C.

By using the catalyst of the present invention, as shown, for example, in Example 1, the yield of octahydro acridine pyridine is 50.6% when the conversion of cyclic ketone was 69.7 wt %. The yields being shown as the value calculated based on the conversion of cyclic ketones. The present invention is described below in more detail referring to Examples, to which the present invention is not limited.

EXAMPLE 1

According to J. S. Beck et al, Nature 359 (1992) 710, mesoporous molecular sieve MCM-41 was synthesized as follows.

Solution A was prepared by mixing 0.38 g of NaOH, 20 ml of water, 0.76 g of Aluminium isoproxide and heated till a clear solution was obtained. After this 9.8 ml of Tetra ethyl ammonium hydroxide was added while cooling the mixture.

Solution B was prepared by mixing 11.6 ml (9.6 g) of 50 wt % ludox silica in 50 ml of distilled water the mixture was kept under vigorous stirring until a clear solution formed.

Solution A was added to Solution B under vigorous stirring and kept for stirring for one hour, after that 10.55 g of Hexadecyl trimethyl ammonium bromide (HDTMABr). The pH was adjusted to 10.5.

A stainless steel autoclave having 0.6 liters of volume was charged with the above solution.

The autoclave was sealed and heated to 100° C. Hydrothermal synthesis was effected under this condition while continuing stirring for 20 hours. In this period, the inner pressure of the autoclave was 5 to 6 kg/cm$^2$.

After completion of the reaction, the reaction mixture was cooled to room temperature and the product was separated by filtration. After repetition of washing and filtration until the concentration of Br ion in the filtrate became 1 ppm or below, the product was dried at 110° C. for 16 hours and then calcined in air at 500° C. for 12 hours to elute the surfactant. White crystals of Na form Al-MCM-41 were obtained. As a result of the measurement of X-ray diffraction, the crystals had a diffraction pattern coincident with that of MCM-41 reported in Nature 1992 by Breck et al. After this the catalyst was pelletized and converted to 18–30 size mesh.

EXAMPLE 2

A glass reaction tube having an inner diameter of 20 mm was filled with 4 g of this crystalline Al-MCM-41 catalyst. A mixture of 1moles of cyclohexanone one mole of formaldehyde (40 wt % solution in water) fed on to the packed catalyst through preheating zone in gas form along with ammonia and the temperature maintained 400° C. at the catalyst bed. The reaction products were collected at bottom through ice cold traps and analyzed by a FID gas chromatography. The products were further confirmed $GC_{13}MS$ and NMR.

Average yields of the products in a period of 4 hours from the start of the reaction were found 50.6% of octahydro acridine J. S. Beck et al, Nature 359 (1992) 710, 4.1% of cyclohexyl amine and other products. Another major product is the condensed product of two moles of cyclohexanone and one mole formaldehyde an intermediate in the formation of octahydro acridine.

EXAMPLE 3

The reaction carried out in same manner as in Example 2 with HY catalyst, the selectivity of octahydro acridine (bis cyclohexyl pyridine, 1) is 30.4% at the conversion of cyclohexanone is 82.8 wt %.

EXAMPLE 4

The reaction carried out in same manner as in Example 2 with HZSM-5 (30) catalyst, the selectivity of octahydro acridine is 48.6% and the conversion of cyclohexanone is 79.0 wt %.

EXAMPLE 5

The reaction carried out in same manner as in Example 2 with H-BEA catalyst, the selectivity of octahydro acridine is 40.6% and the conversion of cyclohexanone is 40.6 wt %.

EXAMPLE 6

The reaction was carried out in same manner as in Example 2 except cyclopentanone was used as cyclic ketone instead of cyclohexanone and the final product was bis cyclopentyl pyridine, 2 with selectivity of 31.7 at the 82.7% conversion of cyclopentanone.

EXAMPLE 7

The reaction was carried out in same manner as in Example 2 except cyclo heptanone was used as cyclic ketone instead of cyclohexanone and the final product was bis cycloheptyl pyridine, 3 with selectivity of 44.9 at the conversion of cycloheptanone is 72.2 wt %.

EXAMPLE 8

The reaction was carried out in same manner as in Example 2 except cyclooctanone was used instead of cyclohexanone and the final product was Bis cyclooctyl pyridine, 4 with selectivity 30.5% at the conversion of 75.0 of cyclooctanone.

EXAMPLE 9

The reaction was carried out in same manner as in Example 2 except cyclopentanone and cyclohexanone were used as a mixture instead of cyclohexanone alone and the final product was Bis cyclopentyl hexyl pyridine, 5.

EXAMPLE 10

The reaction was carried out in same manner as in Example 2 except acetaldehyde (35 wt %) was used as aliphatic aldehyde instead of formaldehyde and the final product was 9-Methyl octahydro acridine, 6 with 24.0% and octahydro acridine, is 18.0% selectivity at the 85.5% conversion of cyclohexanone.

EXAMPLE 11

The reaction was carried out in same manner as in Example 2 except propionaldehyde was used as aliphatic aldehyde instead of formaldehyde and the final product was 9-Ethyl octahydro acridine, 7 with 15.5% and octahydro acridine is 16.9% selectivity at the 86.0% conversion of cyclo hexanone.

EXAMPLE 12

The reaction was carried out in same manner as in Example 2 except butyraldehyde was used as aliphatic aldehyde instead of formaldehyde and the final product was 9-propyl octahydro acridine, 8 with 10.5% and octahydero acridine is 7.6% selectivity at the 74.2% conversion of cyclohexanone.

EXAMPLE 13

The reaction was carried out in same manner as in Example 2 except formamide was used instead of formaldehyde and the final product was 9-amino octahydro acridine, 9 with 10.0% and octahydero acridine is 20.0% selectivity at the 50.4% conversion of cyclohexanone

ADVANTAGES OF THE INVENTION

The present invention provides a process that comprises of environmentally clean and economical technology, easily recycled and reusability of the catalyst The process provides an eco-friendly method with high selectivity towards the product.

This method provides a selective heterogeneous catalyst with longer life.

Further, this method provide a route, wherein the kind and composition of annulated pyridines can be varied by varying the starting materials.

It also provides an efficient and economical method for synthesizing octahydroacridine from cyclohexane and formaldehyde with ammonia over mesoporous molecular sieves.

We claim:

1. A process for the synthesis of an annulated pyridine base, wherein said annulated pyridine base is selected from,

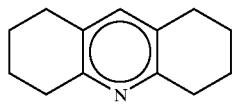

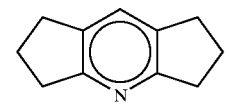

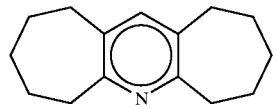

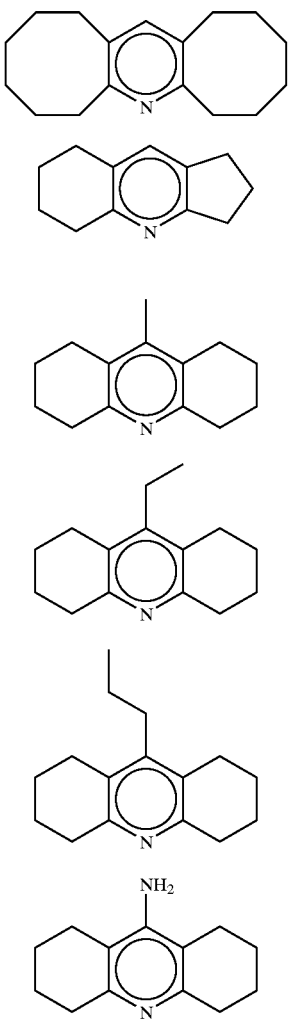

said process comprising reacting a cyclic ketone containing 5 to 8 carbon atoms and an aliphatic aldehyde having the formula $R_1CHO$, wherein $R_1$ is hydrogen or alkyl having 1 to 3 carbon atoms, with ammonia in a gaseous phase in the presence of a mesoporous sieve catalyst to obtain said annulated pyridine base, wherein the mole ratio of ammonia to cyclic ketone is in the range of 0.5 to 5.0 and the reaction temperature is in the range of 350° C. to 450° C.

2. A process as claimed in claim 1, wherein the cyclic ketone is cyclohexanone and the aliphatic aldehyde is formaldehyde to obtain 1,2,3,4,5,6,7,8-octahydro acridine.

3. A process as claimed in claim 2, wherein the cyclohexanone, formaldehyde and ammonia have a molar ratio of 1:1:0.5-5.

4. A process as claimed in claim 3, wherein methanol is added in an amount up to 0.5 mole per mole of cyclohexanone.

5. A process as claimed in claim 1, wherein the temperature of the reaction is in the range of 300 to 400° C.

6. A process as claimed in claim 1, wherein the aliphatic aldehyde is acetaldehyde to obtain 9-methyl octahydro acridine.

7. A process as claimed in claim 1, wherein the aliphatic aldehyde is propionaldehyde to obtain 9-ethyl octaohydro acridine.

8. A process as claimed in claim 1, wherein the aliphatic aldehyde is butyraldehyde to obtain 9-propyl octahydro acridine.

9. A process as claimed in claim 1, wherein the cyclic ketone is cyclopentanone to obtain bis cyclo pentyl pyridine.

10. A process as claimed in claim 1, wherein the cyclic ketone is cyclooctanone to obtain bis cyclooctyl pyridine.

11. A process as claimed in claim 1, wherein the mesoporous sieve catalyst comprises Si and Al in a proportion of 2.5 to 25.

12. A process as claimed in claim 1 wherein the mesoporous sieve catalyst is selected from the group consisting of Al-MCM-41, ZSM-5, HY and H-BEA and mixtures thereof.

* * * * *